United States Patent [19]
Duplan et al.

[11] Patent Number: 5,722,960
[45] Date of Patent: *Mar. 3, 1998

[54] RETRACTABLE NEEDLE SYSTEM

[75] Inventors: Nancy Duplan; Carlton E. Duplan, both of San Marcos, Calif.

[73] Assignee: Duplan Industries, San Marcos, Calif.

[*] Notice: The term of this patent shall not extend beyond the expiration date of Pat. No. 5,304,150.

[21] Appl. No.: 97,989

[22] Filed: Jul. 27, 1993

Related U.S. Application Data

[63] Continuation-in-part of Ser. No. 903,617, Jun. 24, 1992, Pat. No. 5,304,150.
[51] Int. Cl.$^6$ ............................................. A61M 5/00
[52] U.S. Cl. ............................................. 604/195; 604/110
[58] Field of Search .......................... 604/110, 194–198, 604/218, 239–240, 243

[56] References Cited

U.S. PATENT DOCUMENTS

| | | |
|---|---|---|
| 4,969,877 | 11/1990 | Kornberg et al. |
| 4,978,340 | 12/1990 | Terrill et al. ............... 604/195 |
| 5,098,390 | 3/1992 | Wallingford et al. |
| 5,152,750 | 10/1992 | Haining .................... 604/195 |
| 5,180,370 | 1/1993 | Gillespie .................. 604/110 |
| 5,304,150 | 4/1994 | Duplan et al. ............. 604/195 |
| 5,344,403 | 9/1994 | Lee .......................... 604/110 |

FOREIGN PATENT DOCUMENTS 2137405  2/1973  Germany.

*Primary Examiner*—Corrine M. McDermott
*Attorney, Agent, or Firm*—Morrison & Foerster LLP

[57] ABSTRACT

A retractable needle system for use with a medical device is described. The system uses a retractor which engages the well of a needle support means and retracts the needle support means containing the needle back into the cylindrical barrel of the medical device.

4 Claims, 9 Drawing Sheets

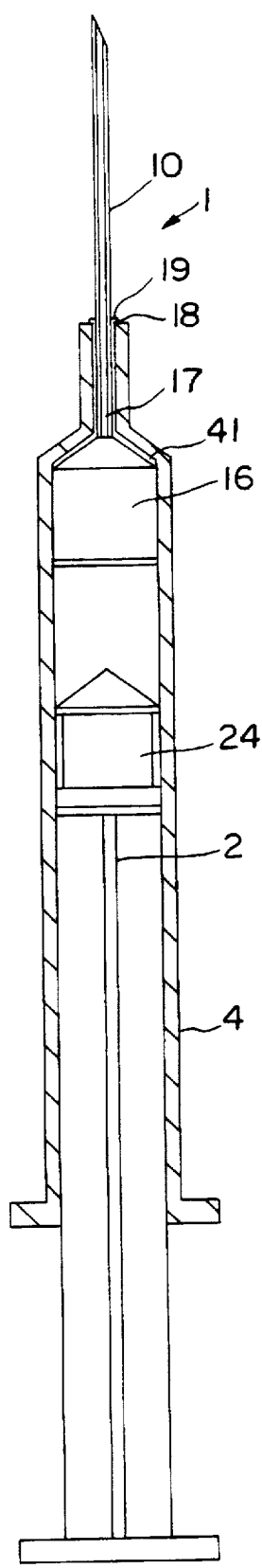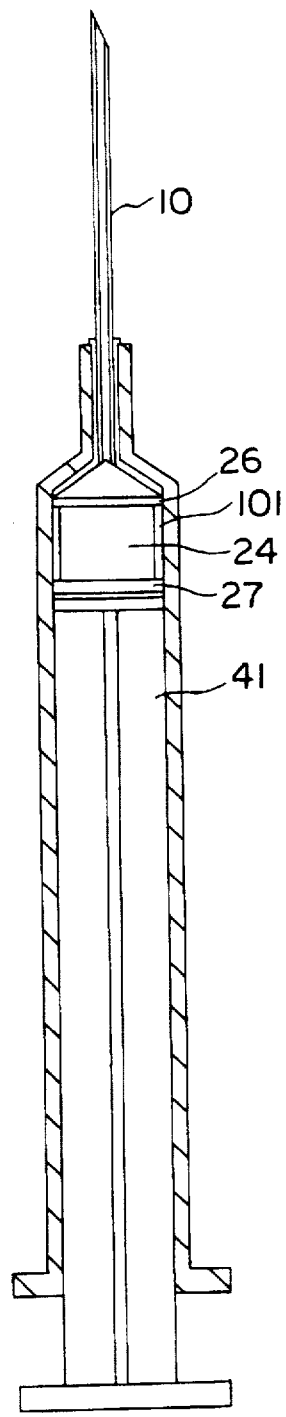
FIG. 5
FIG. 6

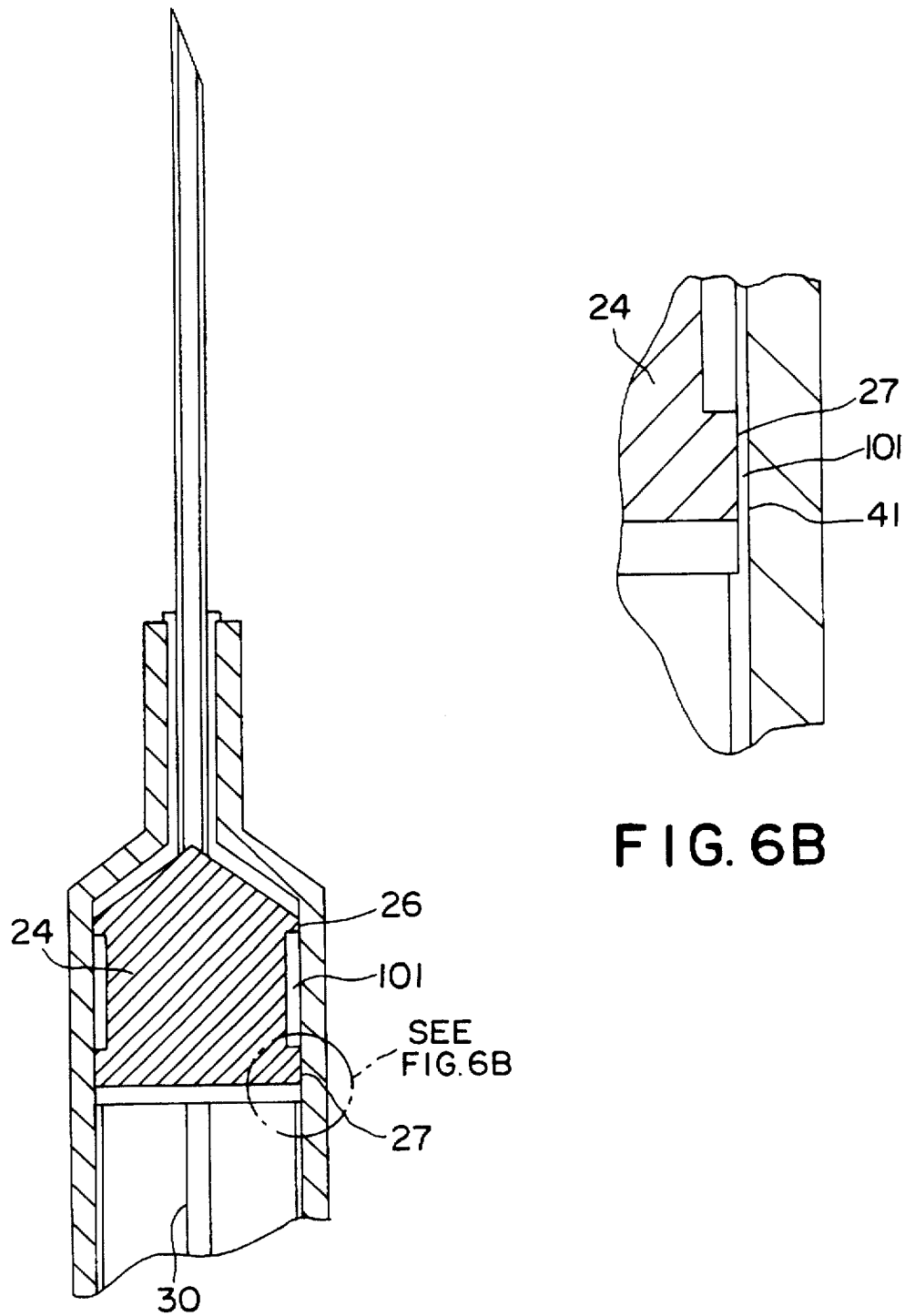

RETRACTABLE NEEDLE SYSTEM

RELATED APPLICATION DATE

This application is a continuation-in-part of commonly-owned and application Ser. No. 07/903,617 filed Jun. 24, 1992 now U.S. Pat. No. 5,304,150.

TECHNICAL FIELD

The present invention relates to hypodermic needles which can be retracted into a medical instrument, such as the barrel of a syringe, or of a VACUTAINER cup holder, after use.

BACKGROUND OF THE INVENTION

Hypodermic needles are common instruments utilized daily in the practice of medicine. Such needles find use primarily in conjunction with associated medical instruments, e.g., syringes, blood collection devices, intravenous tubing and the like. Disposable needles are among the most frequently used hypodermic needles.

After use, the needle is often subject to further handling before disposal. There is an ongoing concern among medical personnel to prevent the spread of infectious diseases by avoiding contact with contaminated needles before they are discarded. Although medical personnel are generally well informed of the dangers and diligent in following proper disposal procedures, the stress of providing medical care in emergency cases inevitably causes occasional mishaps.

Therefore, it is presently considered desirable to provide a hypodermic needle which can be quickly and easily sequestered after use to prevent unintended contact. One approach is to provide a hypodermic needle which can readily be withdrawn into the associated medical instrument after use.

U.S. Pat. Nos. 4,969,877 and 5,098,390 disclose syringes with retractable needles. However, these designs are specialized and complex. They are expensive to manufacture and do not lend themselves to application to standard medical instruments.

DISCLOSURE OF THE INVENTION

The present invention provides a retractable needle system for use with associated medical devices that is simple to manufacture, compatible with standard medical devices, and easy to use. The retractable needle system is designed to retract a hypodermic needle into the cylindrical barrel of a device such as a syringe or blood sampling device, and comprises a needle support means and a retractor means. The needle support means has a shape designed to conform to the forward end of the cylindrical barrel and has a means for mounting a needle and a well that has an exterior surface configured to provide sealing engagement with the interior forward surface of an associated medical instrument and an interior surface configured to provide a sealing engagement with the retractor. The retractor is designed so as to move freely within an associated medical device, such as a syringe barrel or a VACUTAINER tube holder for extraction of blood. The forward end of the retractor comprises a sealing means to provide irreversible sealing engagement with the interior surface of the well of the needle support means. A hypodermic needle can be operatively mounted on the needle support means. The invention also provides syringes and blood collection devices containing the retractable needle system of the invention.

BRIEF DESCRIPTION OF THE DRAWINGS

FIGS. 2A and 2B are expanded views of the positive locking engagement between the needle support means and the retractor.

FIG. 5 shows a cross sectional view of a second embodiment of the invention placed within the barrel of a standard syringe.

FIGS. 6, 6A and 6B show cross sectional views of the embodiment of FIG. 5 with the retractor of the invention fitted within the interior of the well of the needle support. FIGS. 6A and 6B are expanded views of the friction-locking engagement between the needle support means and the retractor.

FIG. 8A shows a cross sectional view of the well of the needle support means showing a flap 102 which protrudes into the interior of the well; FIG. 8B shows a cross section looking down through the well and depicting the protrusion of the flaps 102 into the interior surface.

MODES OF CARRYING OUT THE INVENTION

Figure 1:
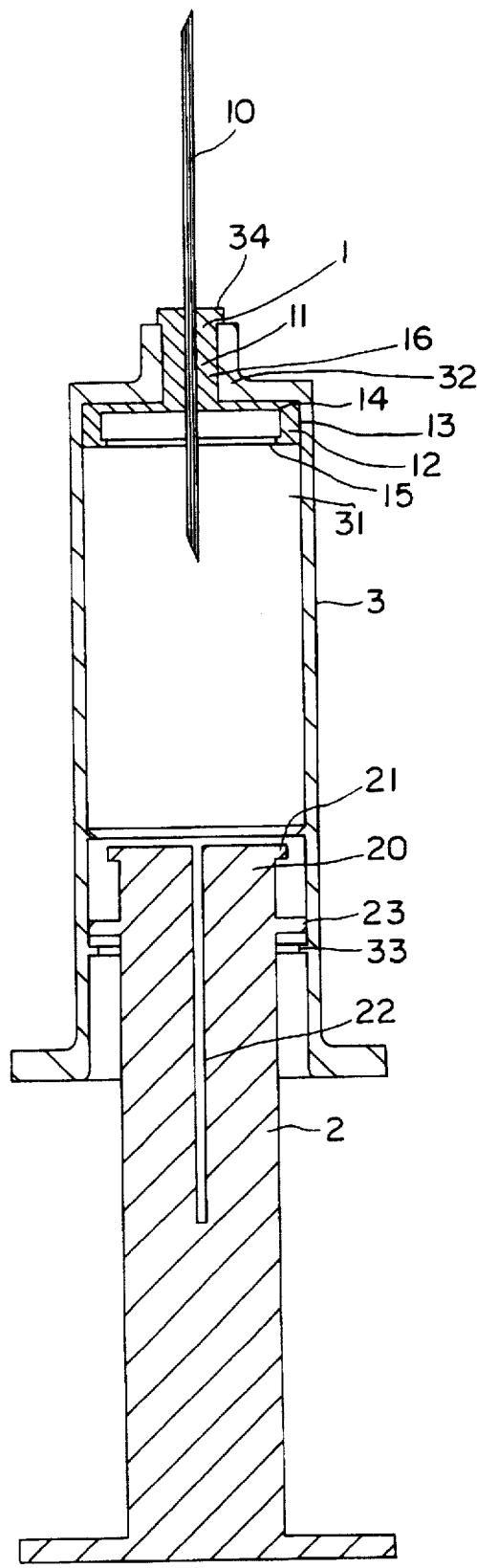
FIG. 1 shows a cross-sectional view of one embodiment of the invention placed within the holder for a commercially available blood collection device.

The retractable needle system of the invention is designed to retract a hypodermic needle into the typically cylindrical barrel of a standard medical device such as a syringe or a tube holder for blood collection. The system is simple to construct and works on the principle of providing a needle support means which conforms to the front end of the cylindrical barrel of a medical device and is adapted to contain the appropriate hypodermic needle. The needle support means has a well that can be essentially irreversibly engaged by the front end portion of a retractor. The retractor my specifically be designed for this purpose or may serve, also, as the plunger in a syringe. The needle support means contains a well into which the front end portion of the retractor can be fitted. When the retractor front end is inserted into the well, an essentially irreversible engagement of the retractor with the needle support means is obtained. The ability to insert the front end of the retractor into the well and still provide this irreversible engagement resides in the use of a compressible material for the construction of either the well or the front end of the retractor or both. The compressible material allows for insertion of the front end of the retractor, but the elasticity of the material results in irreversible engagement once the retractor is inserted.

By "irreversible engagement" is meant that the front end of the retractor will stay inserted in the well of the needle support means when the retractor is withdrawn into the cylindrical barrel of the medical device. By "reversible sealing of the needle support means to the front end of the cylindrical barrel" is meant that the needle support means will stay in place during normal use of the medical device until engaged by the retractor and withdrawn through the cylindrical barrel.

In one embodiment, both the well of the needle support means and the forward end of the retractor are provided with an annular ridge. Both components are constructed of materials that are sufficiently flexible to allow the ridges to slide past each other when the retractor is inserted into the needle support means well, applying moderate pressure by the operator, but sufficiently rigid to interlock the ridges when the retractor is withdrawn into the barrel. Thus, the force required to unlock the ridges is greater than the force required to slide the needle support means by means of the retractor back into the barrel. In another embodiment, the well of the needle support means contains a smooth interior surface and the compressible materials are provided by the forward end of the retractor. In this embodiment, the needle support means can be made of any arbitrary material, such as metal or plastic, but the forward portion of the retractor must be made of a synthetic material which is capable of compression to allow insertion and then re-expansion to exert an adhesive pressure against the wall of the well. In one particularly preferred embodiment, the well may be provided with "flaps"—i.e., u-shaped, thicker cutouts from the surface which provide additional gripping power.

In one illustrative embodiment of the invention, the retractable needle is adapted for use with a blood collection device, such as a VACUTAINER tube holder. In general, such a commercially-available blood collection device will consist of a cylindrical barrel with a forward end into which a needle can be inserted. Located on the axis of this forward end is a narrow tip projection which serves as a mounting point for a needle support means designed to accommodate a conventional double-ended hypodermic needle which acts to provide a channel for the liquid drawn through the needle into the VACUTAINER tube by an externally applied vacuum source. The barrel will also include a rearward end having a port wherein the VACUTAINER tube that supplies the vacuum is inserted into the barrel. The rearward end will also have flanges configured to provide support for the operator's fingers.

As shown in FIG. 1, the VACUTAINER tube holder 3 is fitted with the retractable needle system 1 of the invention. The needle 10 to be retracted 10 is typically pointed at each end and is inserted into the needle support means so as to extend from either end. The needle is securely contained in needle support means and securely sealed into the forward portion 11 (needle-engaging means 1) thereof.

The needle support means shown has a well 12 with an exterior surface 13 designed to provide a reversible sealing engagement with the interior surface 31 of the VACUTAINER tube holder 3. The well 12 of the needle support means 1 also contains an interior surface 14 designed to provide a sealing engagement with the front end 20 of the retractor 2. This may be aided by flange 15 extending into the lumen of the well of the needle support means 1.

The retractor 2 is generally a plunger having at its forward end 20 at least one annular flange or ridge 21 which is capable of providing a sealing engagement with the interior surface 14 of the needle support means 1. The retractor 2 also has a recessed portion 22 designed to accommodate the rearward extension of the needle when the retractor is engaged with the needle support means.

Figure 2:
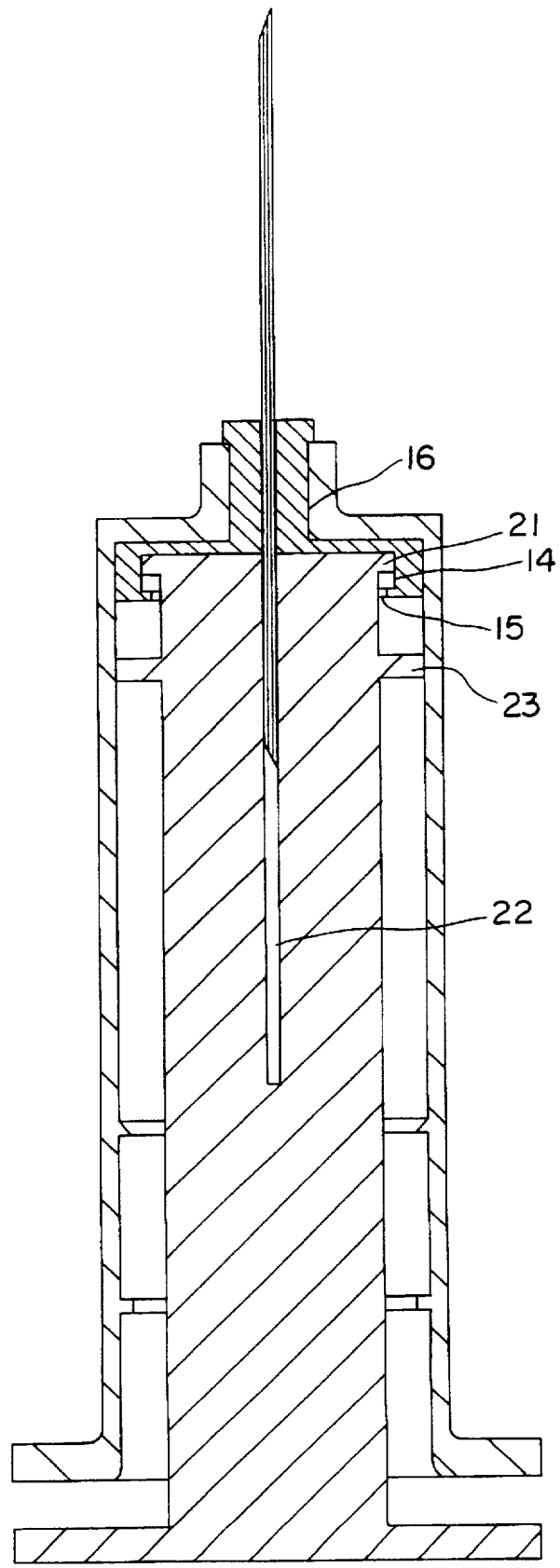
FIGS. 2, 2A and 2B depict cross-sectional views of the embodiment of FIG. 1 with the retractor of the invention fitted within the interior surface of the well of the needle support.
Figure 2B:
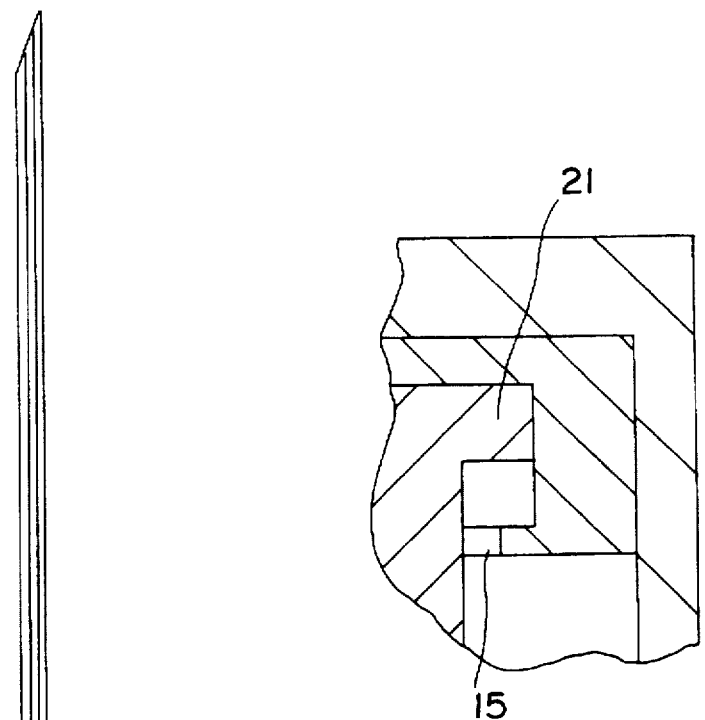
Figure 2A:
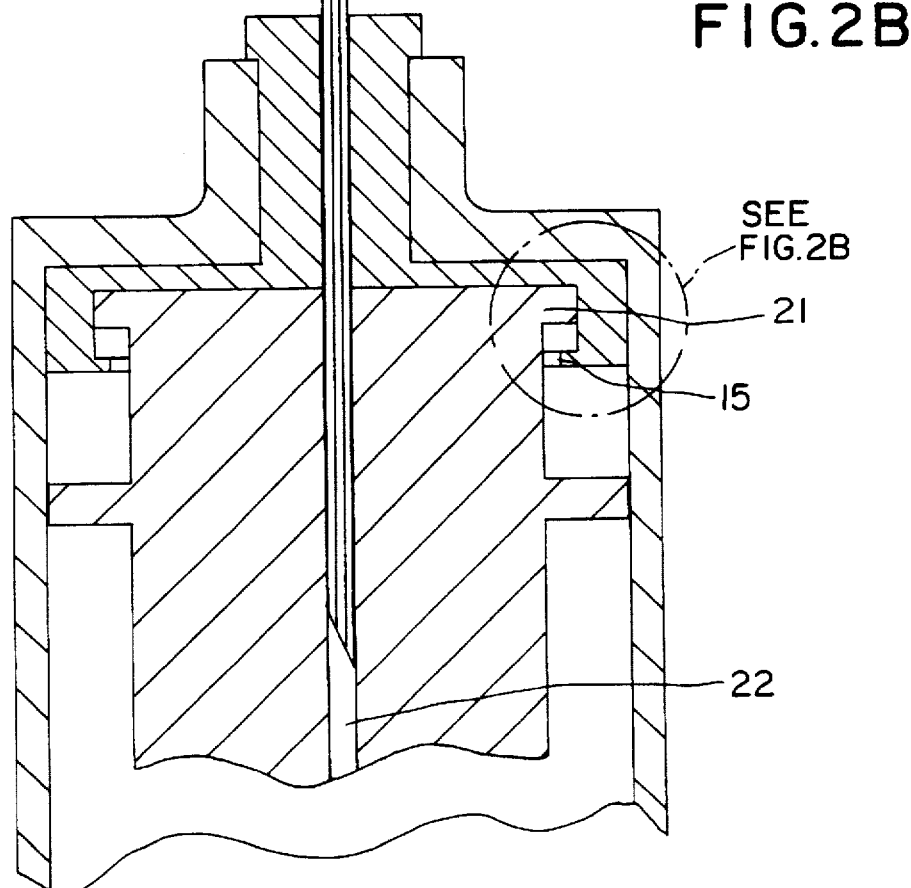

FIG. 2 shows the apparatus of FIG. 1 with the retractor engaged with the needle support means. As shown in FIG. 2, annular ridge or flange 21 provides "irreversible" sealing engagement with the interior surface 14 of the needle support means 1 and is further engaged by the flange 15. FIGS. 2A and 2B show enlarged views of this engagement. The needle 10 is accommodated by the recessed portion 22.

Figure 3:
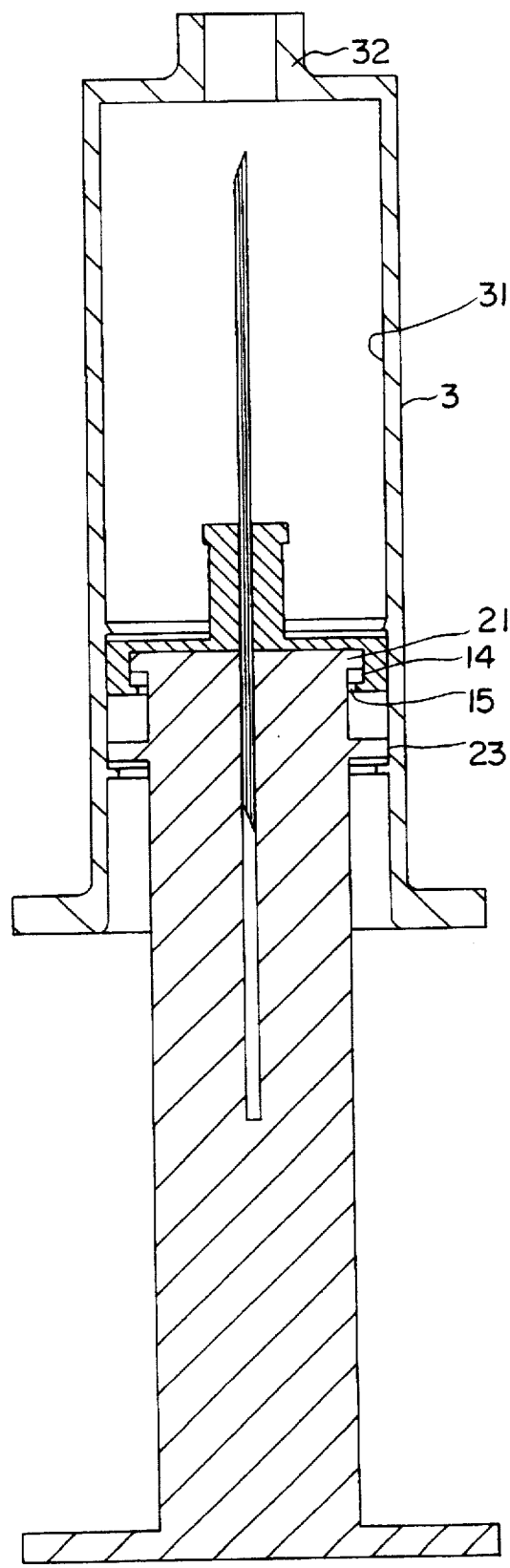
FIG. 3 depicts the needle support means and its attached needle withdrawn by the retractor into the barrel of the blood collection device in the embodiment of FIG. 1.

FIG. 3 shows the device of FIGS. 1 and 2 with the needle retracted into the cylindrical barrel of the tube holder. The flange 33 extending into the lumen of the tube holder at its rearward end arrests the backward motion of the engaged needle support and retractor.

The exterior diameters of needle support means 1 are established such that a loose interference fit will exist between the support means and the interior surface 31 of holder barrel 3 and its forward extension 32. The tolerances will be established such that the needle support will not slide with respect to the holder until a sufficient force is applied to the retractable needle support means by the retractor. The needle can thus be manipulated while it is inserted into the vein of a subject from whom blood will be drawn.

In certain embodiments, it may be considered desirable further to reduce any tendency of the needle support means to slide into the holder barrel when pressure is applied to needle, such as when the needle meets resistance in puncturing the skin of a patient. This objective can be accomplished, for example, by including certain structural features in the needle support means in order to enhance the interlocking engagement between needle support means and barrel of the holder. For example, as depicted in FIG. 1, the portion of the needle support means which engages and surrounds needle (the needle securing means) can be extended 11 along the length of needle 10 to a point where it will project through the fluid port 16 and out of the holder barrel at the forward end of extension 32 when the needle is fully engaged. The forward end of this extension can be configured with an annular ridge 34 such that the exterior diameter of the extension at ridge is slightly larger than the interior diameter of the fluid port 16 of holder barrel. In this manner, once the needle is fully engaged with barrel of the holder, a positive locking engagement is established. This feature increases the force which would be necessary to disengage the needle from holder barrel.

When the retractor is engaged with the needle support means as shown in FIG. 2, the force required to initiate movement between needle support means and inner surface of the holder barrel ($F_1$) is less than the force required to initiate movement between the retractor and the needle support means ($F_2$). This permits the retractor to pull the needle support means back into the tube holder barrel. Various means in addition to that shown in FIGS. 2, 2A and 2B are available to assure that $F_2 > F_1$. For instance, roughening either interior surface of needle support means or exterior surface of the forward end of retractor would increase $F_2$. It is considered desirable to effect such a modification on needle support means, in order to readily adapt the present device to a wide range of commercially-available holders without requiring modification thereof. Such roughening of interior surface can be achieved in any conventional means, such as mechanically, chemically or by various well-known molding techniques, which produce a textured surface.

The structural features shown in FIGS. 2, 2A and 2B can be incorporated into the retractable needle system in order to enhance the interlocking engagement between needle support means and the forward end of the retractor. The rearward end of the well of the needle support means is configured with an annular ridge or flange 15 so that the effective interior diameter of needle support at the ridge is smaller than that of the forward flange 21 at the forward end of retractor. The remaining diameter of the annular portion of the needle support means will be sufficient to accept the forward end of retractor. In this manner, once the forward end of retractor is engaged with the rearward end of needle support means, a positive locking engagement is established (FIGS. 2, 2A, 2B). This feature greatly increases the force ($F_2$) which would be necessary to disengage the retractor from the needle support means. As stated above, the flanges must be constructed of a material which is sufficiently flexible to allow them to engage when the retractor is moved forward, but sufficiently rigid so that they do not disengage when the retractor is withdrawn. Such materials as flexible aluminum, polypropylene or other plastics or modified rubber materials may be used. The width of each flange is adjusted so that it is possible for them to slide past each other when the retractor is moved forward but to engage when the retractor is withdrawn. In addition, the spacing of flange 15 from the bottom of the well is such that the depth of flange 21 can be accommodated between flange 15 and the bottom of the well.

As shown in FIG. 2, the retractor is inserted into holder barrel in such fashion that the forward end engages the rearward end of needle support means. The holder is of sufficient length to allow full retraction of the needle into the barrel of the tube holder before coming to rest at flange 33.

Figure 4:
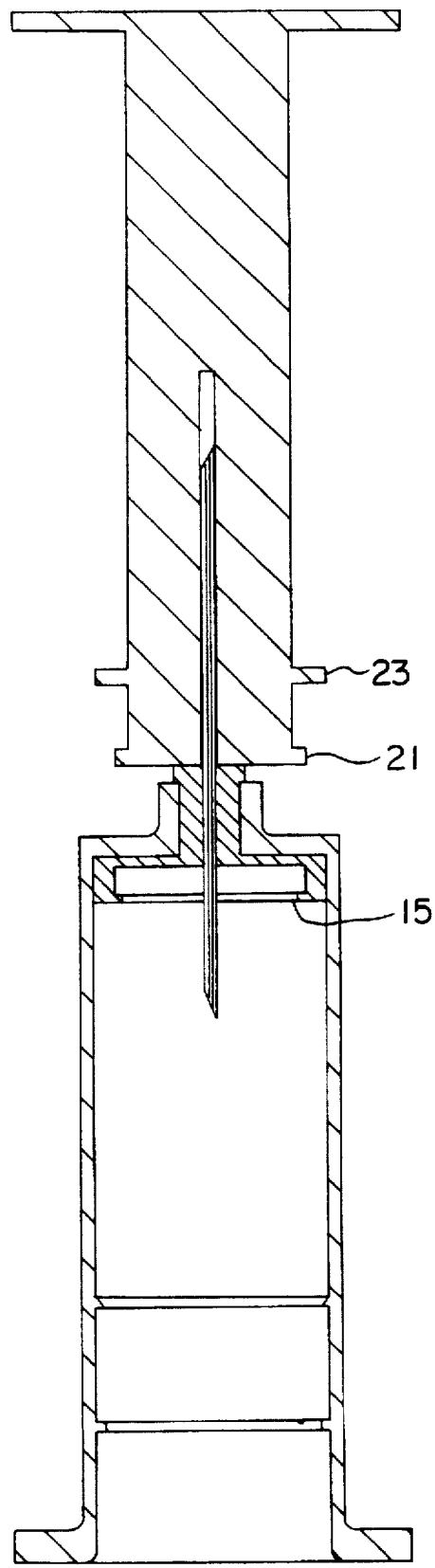
FIG. 4 shows an embodiment of FIG. 1 as it might be packaged for sale.

In use, the retractable needle system containing a needle of the present invention can be installed in the holder at the site of manufacture and the hypodermic needle can be covered with any conventional needle guard. Alternatively, as the forward end of retractor will generally include a needle recess, the retractor can be utilized as a needle guard in certain embodiments as shown in FIG. 4.

The operation of the present invention will be described with reference to FIGS. 1–3. As shown in FIG. 1, once the blood collection device has been used, and the VACUTAINER tube withdrawn from the holder barrel, the retractor is inserted as shown in FIG. 1 and pressed forward as shown in FIG. 2, causing the forward end to engage with the rearward end of needle support means and establish locking engagement.

Once this engagement is established, the retractor is withdrawn into the barrel with a force greater than $F_1$ but less than $F_2$ so as to draw the needle support means and attached hypodermic needle into the holder barrel for subsequent disposal.

Figure 7:
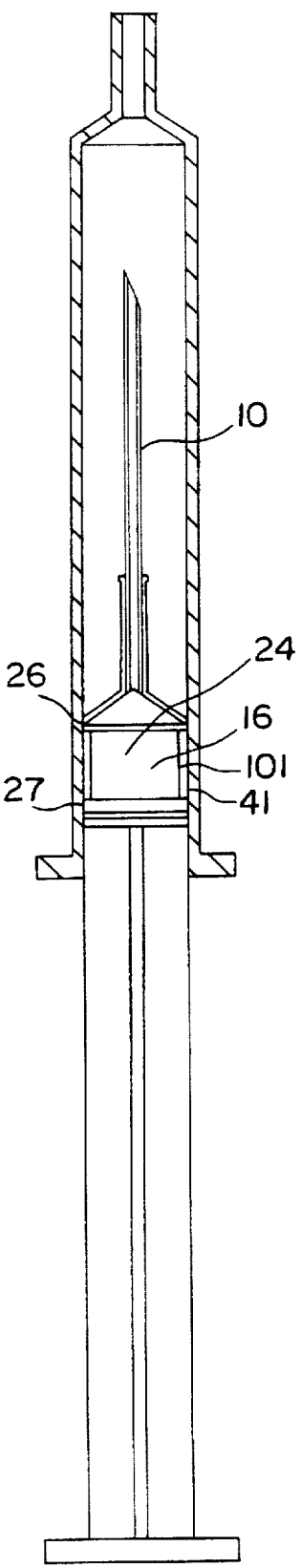
FIG. 7 shows the needle support means and its attached needle withdrawn by the retractor into the barrel of the syringe in the embodiment of FIG. 5.

As depicted in FIGS. 5–7, another embodiment of the present invention is shown as a retractable needle system for a syringe. The system comprises a needle support means 1, shown with a needle 10 mounted in it, optionally, constructed of metal. The needle and support means may be formed integrally, or needle support means can be formed from any rigid material to facilitate ease of manufacture. As above and shown now in FIG. 5, needle support means contains a means for mounting the needle 17 and a well 16 that conforms to the interior dimensions of the syringe barrel 4 and desirably includes a conical converging forward end which is adapted to establish a fluid-tight seal with forward end of the interior 41 of syringe barrel. Such a seal can be established, for example, by careful control of the dimensions of needle support means, by including a sealing feature in the forward end or by constructing needle support means of a compliant material. The needle is securely fixed to, or releasably secured to, the forward end of needle support means at the apex of the converging cone, so as to align with the fluid release port of the syringe barrel.

The exterior diameters of needle support means, including the forward extension 17 is established such that a loose interference (reversible) fit will exist between the support and the interior surface of syringe barrel. In addition, the tolerance will be established such that there exists an arrangement between needle support means and syringe barrel which prevents one from sliding with respect to the other until a sufficient force is applied to the support means.

In certain embodiments, it may be considered desirable to reduce the tendency of the needle support means to slide into the syringe barrel when pressure is applied to needle, such as when the needle meets resistance in puncturing the skin of a patient. This objective can be accomplished, for example, by including certain structural features into the needle support means in order to enhance the interlocking engagement between needle support means and barrel of the syringe. For example, as depicted in FIG. 5, the portion of the needle support means 1 which engages and surrounds needle 10 is extended along the length of needle to a point where it will project through the fluid release port and out of syringe barrel when needle is fully engaged. The forward end 18 of this extension 17 can be configured with an annular ridge 19, such that the exterior diameter of the extension at ridge is slightly larger than the interior diameter of the fluid release port of syringe barrel. In this manner, once retractable needle is fully engaged with barrel of the syringe, a positive locking engagement is established. This feature increases the force which would be necessary to disengage retractable needle from syringe barrel.

As also illustrated in FIG. 5, the present needle support means will be substantially hollow so as to provide an interior surface which has a rearward end which forms a well 16 having an interior surface 101 and is adapted to accept the sealing portion 24 of the retractor 2 in this case, the hypodermic syringe plunger. (This engagement would be generally as depicted in FIG. 6.) The well will be provided with a fluid communication relationship with hypodermic needle so that any liquid contained within syringe barrel can be dispensed via interior region and through needle when plunger is depressed.

In prior art disposable syringes, the plunger is preferably formed of a material which has a low coefficient of friction, such as a nylon or rubber material, and is generally dimensioned so as to be easily slidable along the interior surface of syringe barrel, while maintaining a fluid-tight seal. In the present invention, the interior region of the well of needle support means will be dimensioned so that the forward end of the retractor will form a tight interference fit with inner region of the support.

The interference fit arrangement between the exterior surface of retractor and the interior surface of well of the needle support, the optional positive locking engagement feature described above, as well as the types of the materials chosen for their construction, allow for the achievement of a predetermined value in the forces required to withdraw the need support means into the syringe barrel.

As above, when the retractor is inserted into the well of the needle support means as shown in FIG. 6, the force required to move the needle support means backwards in the syringe barrel must be less than the force required to remove the forward end of the retractor from the well of the needle support means. Thus, the exterior surface of the needle support means is reversibly engaged with the syringe barrel while the forward end of the retractor is irreversibly sealed, in the sense noted above, to the interior surface of the well. In the embodiment shown in FIGS. 5–7, this is achieved by providing a high value of friction between the configured forward portion of the plunger with respect to the interior of the well. This can be achieved by providing annular flanges 26 and 27 as shown in FIG. 6 which are sufficiently compressible to allow entry of the forward end of the plunger into the well but are capable of re-expansion so as to adhere to the interior walls of the wells. The force of adherence, largely frictional, is such that the force required to dislodge the forward portion of the retractor from the well is greater than the force required to withdraw the needle support means into the barrel of the syringe. This balance of forces is obtained through the design of the physical configuration of the forward end of the retractor in relationship to the interior surface of the well as well as choosing appropriate materials with expansion and compression characteristics that meet these requirements. Most preferred are plastics such as polypropylene and polystyrene.

Figure 8A:
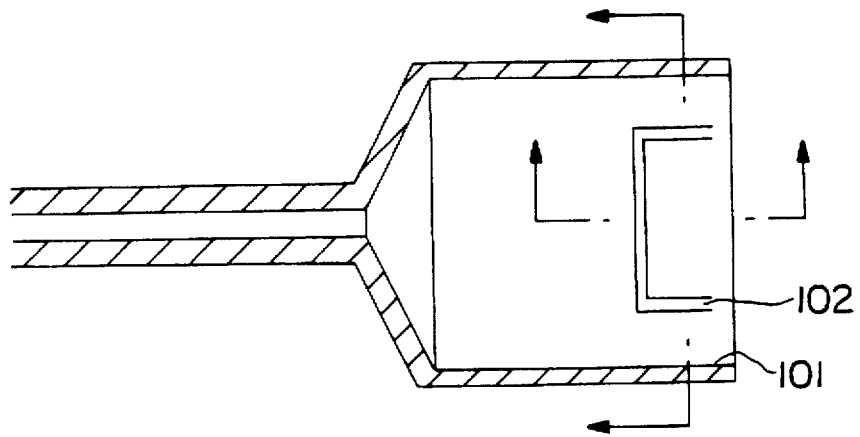
FIGS. 8A and 8B show a modification of the needle support means in the embodiment shown in FIG. 5.
Figure 8B:
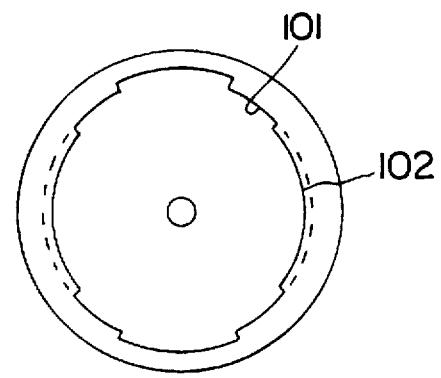

One particular design feature useful for this purpose is shown in FIGS. 8A and 8B. In this design, the interior of the well is modified by providing "flaps" 102 which bulge into the lumen of the well. The well in this case is constructed of a plastic, and the flaps are thus capable of exerting additional inward pressure on the forward portion of the plunger of the syringe.

The operation of this embodiment is shown in FIGS. 5–7. As shown in FIG. 5, the syringe, filled with a material to be injected, is provided with the plunger extended. The needle is placed into the muscle or vein of the subject and the plunger pushed forward so as to expel the injectable material and to engage the needle support means as shown in FIG. 6. The retractor is then withdrawn carrying with it the needle support means and the needle as shown in FIG. 7.

Thus, it can be seen that the present invention provides a novel and improved retractable needle for use with medical instruments, including blood collection devices such as VACUTAINER tube holders or syringes, providing for safe disposal while minimizing the risk of inadvertent contact with a contaminated needle. In addition, the present retractable needle system can be constructed and assembled in a manner which readily adapts to commercially-available tube holder and syringe technology.

We claim:

1. A medical device comprising a retractable needle system and a substantially cylindrical barrel with a front end and a back end, wherein said retractable needle system comprises:

a) a needle for insertion into a patient to administer injectable material or to remove fluid substances;

b) a needle support means supporting said needle, said needle support means being reversibly fastened to the barrel such that the needle is oriented to project outwardly from the front end of the barrel; and c) a retractor capable of being disposed within said barrel and traversing the interior of the barrel, said retractor capable of engaging said needle support means and withdrawing said needle support means and said needle into the barrel as said needle is removed from a patient wherein:

(i) said needle support means comprises a well having a bottom and sides and an exterior surface and an interior surface, said exterior surface being conformed so as to reversibly attach and seal said needle support means to the front end of said cylindrical barrel and said needle support means further containing at the bottom a means for mounting said needle in said needle support means to so as to project said needle from said cylindrical barrel, said needle being in fluid communication therewith;

(ii) said retractor comprises a shank portion which is capable of being disposed within said barrel and traversing between the front end and back end of said cylindrical barrel, said retractor having a front end which is configured so as to irreversibly engage the interior surface of the well of said needle support means when advanced to the front end of said cylindrical barrel, and to thereby retract said needle support means into said cylindrical barrel when the retractor is withdrawn toward the back end of the cylindrical barrel; and (iii) the front end of said retractor is sufficiently laterally compressible to permit insertion of said retractor into the well and sufficiently laterally expandable to produce adhesion between said front end of the retractor and the interior surface of the well, so that when the retractor is withdrawn toward the back end of the cylindrical barrel, the front end of the retractor remains engaged with said needle support means, and withdraws said needle support means into the barrel.

2. The medical device of claim 1, wherein said barrel is a barrel of a hypodermic syringe.

3. A medical device comprising a retractable needle system and a substantially cylindrical barrel with a front end and a back end, wherein said retractable needle system comprises:

a) a needle for insertion into a patient to administer injectable material or to remove fluid substances;

b) a needle support means supporting said needle, said needle support means being reversibly fastened to the barrel such that the needle is oriented to project outwardly from the front end of the barrel; and c) a retractor capable of being disposed within said barrel and traversing the interior of the barrel, said retractor capable of engaging said needle support means and withdrawing said needle support means and said needle into the barrel as said needle is removed from a patient wherein:

(i) said needle support means comprises a well having a bottom and sides and an exterior surface and an interior surface, said exterior surface being conformed so as to reversibly attach and seal said needle support means to the front end of said cylindrical barrel and said needle support means further containing at the bottom a means for mounting said needle in said needle support means to so as to project said needle from said cylindrical barrel, said needle being in fluid communication therewith;

(ii) said retractor comprises a shank portion which is capable of being disposed within said barrel and traversing between the front end and back end of said cylindrical barrel, said retractor having a front end which is configured so as to irreversibly engage the interior surface of the well of said needle support means when advanced to the front end of said cylindrical barrel, and to thereby retract said needle support means into said cylindrical barrel when the retractor is withdrawn toward the back end of the cylindrical barrel; and (iii) the sides of the well of the needle means and/or the front end of said retractor has a sufficiently toughened surface to produce adhesion between said front end of the retractor and interior surface of the well so that when the retractor is withdrawn toward the back end of the cylindrical barrel the front end of the retractor remains engaged in said needle support means and withdraws said needle support means into the barrel.

4. The medical device of claim 3, wherein said barrel is a barrel of a hypodermic syringe.

* * * * *